(12) United States Patent
Wolf et al.

(10) Patent No.: US 9,841,380 B2
(45) Date of Patent: Dec. 12, 2017

(54) METHOD AND APPARATUS FOR DETECTING AND DISCRIMINATING BIOLOGICAL FROM NON-BIOLOGICAL SPECIES

(71) Applicant: University of Geneva, Geneva (CH)

(72) Inventors: Jean-Pierre Wolf, Geneva (CH); Luigi Bonacina, Saint-Prex (CH); Gustavo Alexandre Subtil Sousa, Geneva (CH)

(73) Assignee: University of Geneva, Geneva (CH)

( * ) Notice: Subject to any disclaimer, the term of this patent is extended or adjusted under 35 U.S.C. 154(b) by 18 days.

(21) Appl. No.: 15/236,510

(22) Filed: Aug. 15, 2016

(65) Prior Publication Data

US 2017/0059488 A1  Mar. 2, 2017

Related U.S. Application Data (60) Provisional application No. 62/209,454, filed on Aug. 25, 2015.

(51) Int. Cl.
| | |
|---|---|
| *G01N 21/64* | (2006.01) |
| *A61B 5/00* | (2006.01) |
| *G01J 3/44* | (2006.01) |
| *G01N 21/63* | (2006.01) |

(52) U.S. Cl.
CPC ..... *G01N 21/6486* (2013.01); *G01N 21/6402* (2013.01); *G01N 21/6408* (2013.01); *A61B 5/0071* (2013.01); *A61B 5/0075* (2013.01); *G01J 3/4406* (2013.01); *G01N 21/636* (2013.01); *G01N 2201/06113* (2013.01)

(58) Field of Classification Search
CPC .......... G01N 21/6458; G01N 21/6408; G01N 21/6486; G01N 2201/06113
See application file for complete search history.

(56) References Cited

U.S. PATENT DOCUMENTS

| | | | | |
|---|---|---|---|---|
| 6,633,662 | B2 * | 10/2003 | Ravkin | G01N 15/1475 382/133 |
| 8,939,966 | B2 * | 1/2015 | Hahn | G01N 21/631 600/476 |

(Continued)

*Primary Examiner* — Marcus Taningco
(74) *Attorney, Agent, or Firm* — Da Vinci Partners LLC; John Moetteli (57) ABSTRACT

This invention concerns the field of sample identification, in particular a method and apparatuses for identifying or discriminating biological species from non biological species, both as individual particles and as components of a composition, by pump-probe fluorescence spectroscopy for time-resolved detection or imaging. The method uses the finding that the UV-induced fluorescence of biological molecules is varied, in particular is depleted, by the addition of visible radiation, whereas this does not occur with non-biological organic molecules. The invention discriminates the fluorescence signals of bio and non-bio particles or species using a differential approach, i.e. the comparison. of the total fluorescence recorded with and without additional visible radiation. This allows to discriminate biological particles comprising aromatic amino-acids (AA), like peptides, proteins, bacteria, viruses, pollens, spores, etc., from non-biological particles, like aromatic (AH) or polyaromatic hydrocarbons (PAH), carbonaceous aerosols, soot, etc.

18 Claims, 4 Drawing Sheets

(56) References Cited

U.S. PATENT DOCUMENTS

2010/0006760 A1* 1/2010 Lee .................... G01N 21/3504
250/338.5
2012/0069332 A1* 3/2012 Frankel .................... G01J 3/10
356/301

* cited by examiner

METHOD AND APPARATUS FOR
DETECTING AND DISCRIMINATING
BIOLOGICAL FROM NON-BIOLOGICAL
SPECIES

CROSS REFERENCE TO RELATED APPLICATIONS

This application claims the benefit of U.S. Provisional Application 62/209,454, filed 25 Aug. 2015, the contents of which are incorporated herein by reference thereto.

COPYRIGHT & LEGAL NOTICE

A portion of the disclosure of this patent document contains material which is subject to copyright protection. The, Applicant has no objection to the facsimile reroduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND AND PRIOR ART

The present invention is related to the field of sample identification, in particular to a method for identifying or discriminating biological species from non-biological species, whether they are individual particles or components of a composition. The invention lies in the field of pump-probe fluorescence spectroscopy for time-resolved imaging. It uses the differences in UV induced fluorescence of biological samples vs. non-biological samples when they are exposed to radiation, in particular the fact that the UV fluorescence of bio particles changes, in particular is depleted, by the addition of visible radiation, whereas the UV fluorescence of non-bio particles does not change, in particular is not depleted, under the same condition.

Similar effects were reported using quantum coherence effects in pump-probe femtosecond experiments as described e.g. in "Pump-Probe Depletion Spectroscopy Discriminates Organic and Biological Molecules" by F. Courvoisier, J.-P. Wolf et al. in App. Phys. Lett. 87(6) 063901 (2005) and some subsequent publications by the same group. These experiments use a femtosecond 266 nm pump laser and a femtosecond 800 nm probe pulse.

This coherent control experiment requires rather complex and expensive equipment and thus limits its use to laboratories or to experimental setups. A main disadvantage of prior art solutions and applications is the necessity to use lasers with extremely short pulse durations, usually in the femtosecond range. Such lasers are sensitive, usually rather expensive, unrugged instruments requiring precise adjustment and cautious handling. Also, they often produce non-linear perturbations and unwanted dispersion in attached fibers and probe media to be investigated, thus complicating measurements and leading to unexact results.

It would thus be advantageous if one could use compact, cost effective and rugged lasers producing longer pulses instead of such sensitive femtosecond devices.

On the other hand it was found that biological organic material like amino-acids or material containing aromatic amino-acids, like peptides, proteins, bacteria, viruses, pollens, spores, as well as other biological species like flavins or NAD/NADH (nicotinamide adenine dinucleotide, a coenzyme), exhibits fluorescence depletion in pump-probe arrangements longer than one picosecond, while non-biological organic material like aromatic (AH) or polyaromatic hydrocarbons (PAH) or containing such hydrocarbons, carbonaceous aerosols, or soot, do not exhibit such fluorescence depletion.

This finding allows to discriminate biological material or particles from non-biological particles by using the pump-probe method/arrangement with a laser producing longer pulses, here meaning pulses longer than one picosecond, preferably in the nanosecond range. Even the use of continuous wave (CW) lasers seems reasonable.

The optical identication of bioaerosols in the atmosphere and their discrimination against combustion related particles is a major issue for real-time, field-compatible instruments. The present invention aims at embedding advanced pump-probe depletion spectroscopy accordingly in such portable equipment.

BRIEF SUMMARY OF THE INVENTION

To summarize, contrary to the known experiments and methods, the present invention makes use of two long, here meaning beyond the vibronic coherence time, overlapping nanosecond laser pulses, one in the UV and one in the visible, to distinguish between biological and non-biological material or particles. The advantages are obvious: simpler, portable equipment, less error sources, more economical, mostly even faster. Even continuous wave (CW) or quasi-CW lasers may be used. The possible use of standard, long pulse, typically nanosecond or more, or even CW lasers opens a wide field of applications.

Advanced discrimination methods are needed since the UV fluorescence spectra of bio- and non-bio hydrocarbons strongly overlap. The difference in radiative lifetimes between some PAH and aromatic amino acids can be used to a certain extent, but not with all PAHs. Furthermore, precise lifetime measurements of individual particles containing a mixture of PAH require sensitive and expensive analyzers as described in "Stroboscopic technique for measurement of fluorescence lifetimes of bacteria and biological interferents" by M. Wlodarwski et al. in Proc. SPIE 6398, 69380L (2006) or in "On-the-Fly Fluorescence Lifetime Determination with Total Emission Detection in HPLC" by M. A. Dvorak et al. in Anal. Chem. 69, 3458-3464 (1997).

As compared to chemical or mass spectrometric methods, the present invention offers the advantages of real-time analysis, it is maintenance-free, needs no consumables, and requires no sampling. In particular, large volumes (of air, clean room atmospheres, or water, etc.) can be analyzed instead of checking randomized probes that should be representative of ensembles.

The invention discriminates the fluorescence signals of bio and non-bio particles using a differential approach, namely the comparison of the total fluorescence recorded with and without the additional visible radiation. This allows to assess individual particles, like in flow cytometry, microscopy, imaging, or single aerosol particle analysis, as well as for ensembles of different particles. In this latter case, the outcome of the measurement provides an estimate of the ratio between aromatic amino acids and non-bio hydrocarbons.

The underlying mechanism for the observed fluorescence depletion in the case of amino acids and the absence of fluorescence depletion in the case of other organic compounds relies the difference in the excited state absorption (ESA) characteristics. From the intermediate excited state $S_1$ (populated by the UV laser), the visible photon re-excite the molecules in some upper lying states $S_n$, which are likely to auto-ionize or dissociate, so that fluorescence is depleted. This is the case of AA, but not for AH and PAH, in which either a. the transition moment $S_1 \rightarrow S_n$ is small or
b. $S_n$ decay non-radiatively to $S_1$, leading to the same final population in $S_1$, and thus, the same fluorescence as for the UV excitation only.

Some examples of applications of the invention are listed below:
1. Discriminating of bioaerosols vs. non-bioaerosols in aerosol spectrometers, e.g. bacteria and combustion related aerosols in air;
2. LiDAR remote sensing that allows the discrimination between bioagents and other fluorescing aerosols used e.g. in defence and civil security applications;
3. Detection of bacteria and pathogens in water;
4. Remote airborne imaging of plankton vs. oil spills on oceans;
5. Remote inspection of biological contamination;
6. Detection of bacteria in oil drilling and oil spill cleaning processes;
7. Contamination of food, food packaging, and soils.

It should be understood however that the present invention is not limited to the above applications, but may be used in any field where a variation of fluorescence, whether depletion or increase, can be observed as discriminating feature of particles or materials.

BRIEF DESCRIPTION OF THE DRAWINGS

In the appended drawings show.

DESCRIPTION OF EMBODIMENTS

Figure 1:
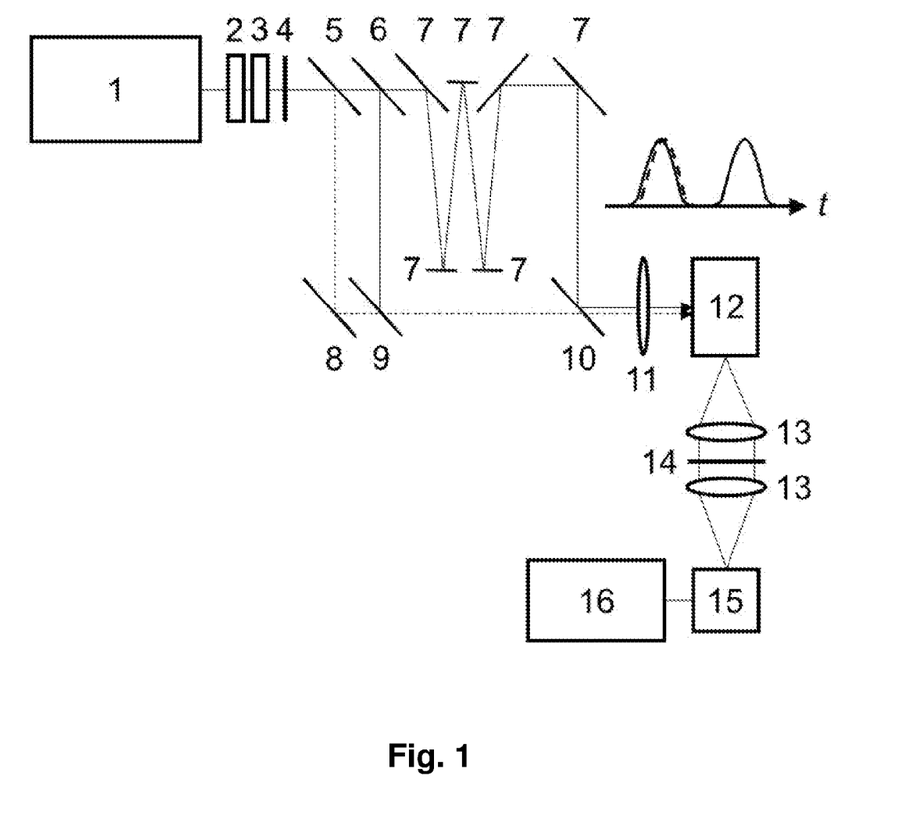
FIG. 1 is a schematic of a first apparatus according to the invention, especially for investigating a flow of aerosol particles.
Figure 2:
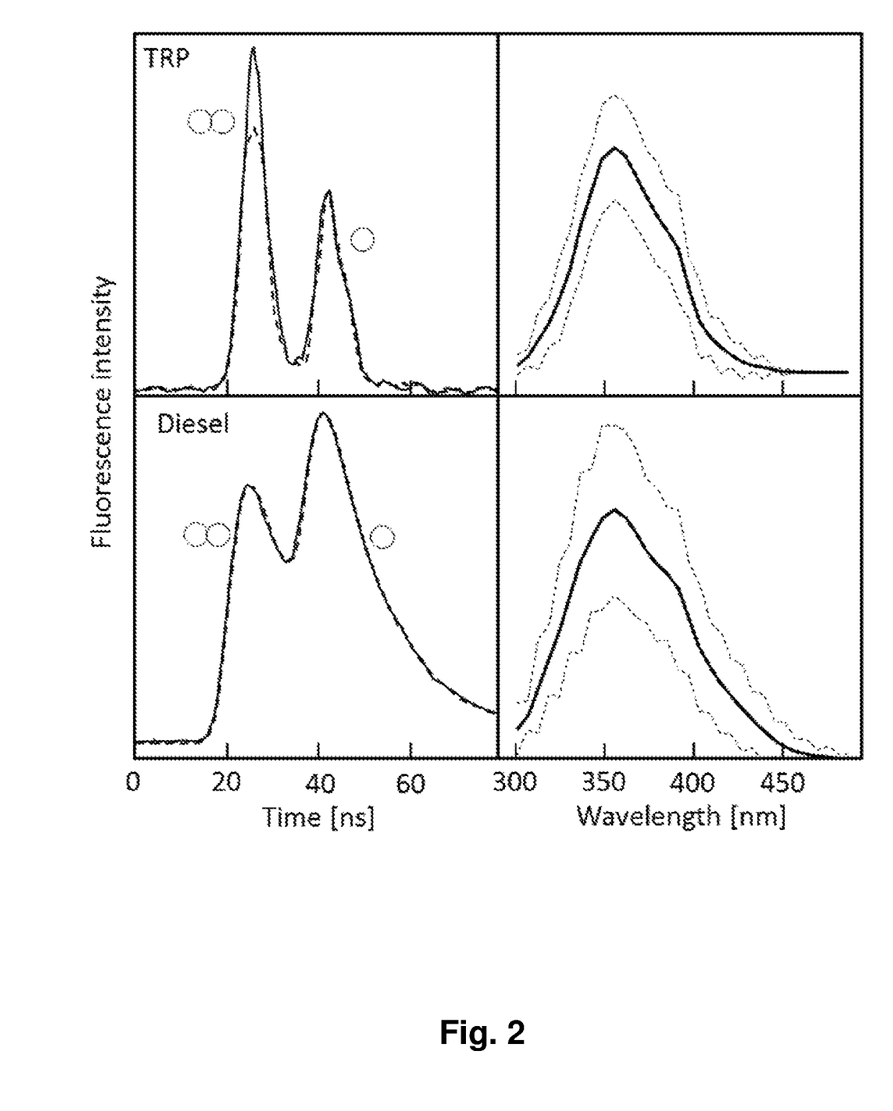
FIG. 2 is a table of fluorescence depletion response vs. fluorescence spectra.
Figure 3:
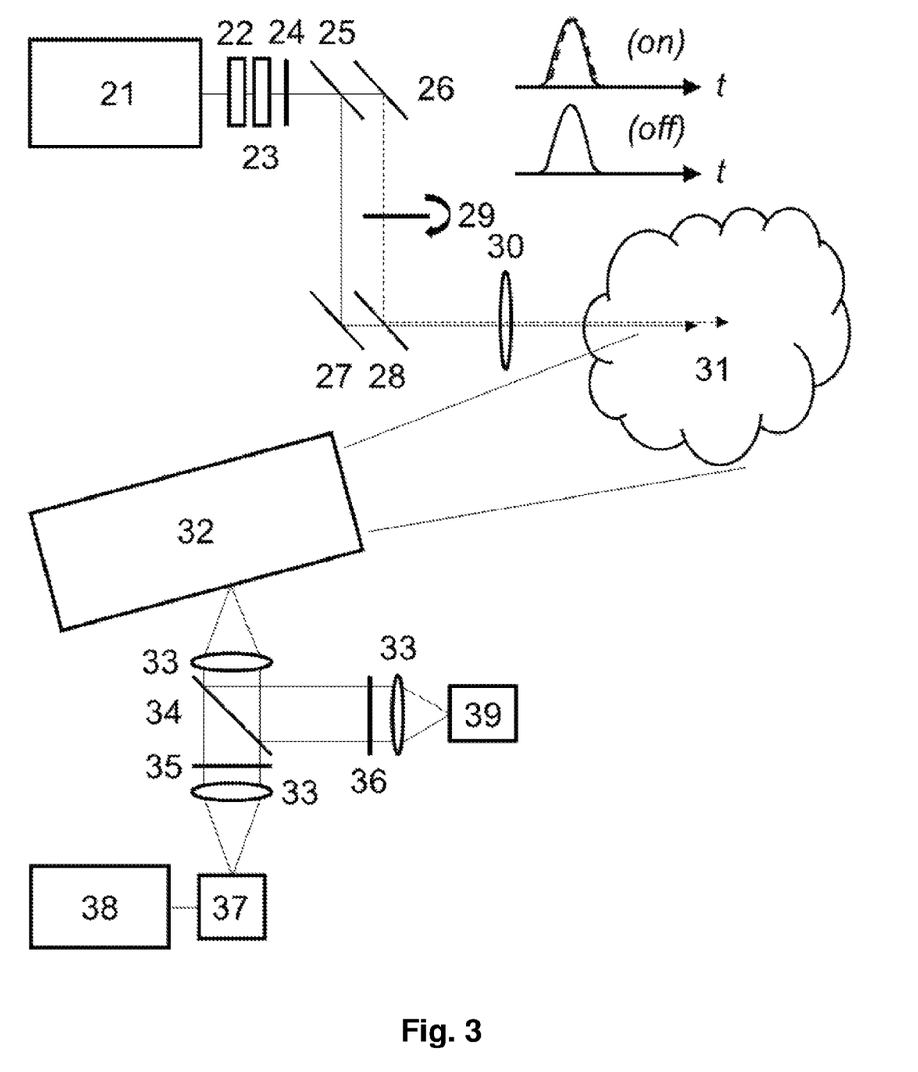
FIG. 3 is a schematic of a second apparatus according to the invention, modified for analysing a mixture of materials.

FIG. 1 shows a first embodiment, i,e. a first practical implementation of the invention, which is geared to discriminate bioaerosols from non-bioaerosols.

FIG. 1 is a schematic illustration. Pulse source is a neodymium-doped yttrium lithium fluoride (Nd:YLF) laser 1 whose laser transitions occur at 1053 nm. The output of this laser 1 is frequency-doubled in a nonlinear crystal 2 providing 527 nm radiation (dashed line in the little diagram) and then frequency quadrupled in a second nonlinear crystal 3 providing 263 nm radiation (full line in the little diagram). The UV polarization is set parallel to the visible by a half wave plate 4. The visible radiation is separated by a first dichroic mirror 5, which transmits 263 nm and reflects 527 nm. The UV of 263 nm is split into two arms by a beam splitter 6, i.e. a partially reflective minor with R=50% at 263 nm. Half of the beam is recombined with the visible radiation of 527 nm by a second dichroic mirror 9. The two radiations are thus temporally overlapped. Optimally, the visible radiation of 527 nm should be slightly shifted by some ns. The second part of the 263 nm UV beam is temporally shifted by typically 20-30 ns by a delay line formed by a set 7 of six high reflectivity (HR) UV mirrors. The delayed UV beam is then recombined with the other two overlapped beams by another UV mirror 10, which reflects 50% of the 263 nm UV and transmits the visible radiation of 527 nm.

The sequence of laser pulses after mirror 10 then has the following time structure:

| Time | Pulse |
|---|---|
| t = 0 | UV radiation 263 nm + visible radiation 527 nm, overlapped |
| +20-30 ns | UV radiation 263 nm only |

In this particular case, each laser pulse has a duration of about 5 ns. This sequence is schematically indicated on FIG. 1 in the little diagram in the right upper corner.

Through focusing lens 11, this laser pulse sequence is focused onto the sample in measuring chamber 12 and produces the desired fluorescence. The sample consists of individual aerosol particles described below.

The produced fluorescence of the sample 12 is collected by a pair of lenses 13, a spectral filter set 14 centered at 340 nm (20 nm FWHM) and rejecting 263 nm and 527 nm, photomultiplier tube 15 and a fast, typical 300-500 MHz, digital oscilloscope interfaced to or integrated into a computer 16.

As mentioned above, this embodiment serves to discriminate bioaerosols from non-bioaerosols. The sample is constituted by an aerodynamically focused flow of aerosol particles, as described, e.g. in L. Bonacina, J.-P. Wolf et al, European Patent Application EP 12167800.7 "Measurement Device and Method for Detection of Airborne Particles", equivalent to U.S. Patent Application 2013/0301047A1 (2013).

The presence of aerosol particles is detected by Mie scattering from additional laser diodes (not shown), and the scatter signals trigger the laser 1. Notice that the sample can also be constituted by a liquid flow cytometer, a liquid (e.g. water) containing biological material and aromatic hydrocarbons, or contaminated surfaces, contaminated food etc.

The discrimination is obtained by comparing the fluorescence signals measured for the combined UV+visible excitation and for the reference UV only excitation, both recorded within the same transient. More precisely, the depletion ratio D (0<D<1) is defined as:

$$D = \frac{F_{UV} - F_{UV+VIS}}{F_{UV}}$$

Where $F_{UV+VIS}$ is the depleted fluorescence intensity and $F_{UV}$ is the undepleted fluorescence. $F_{UV+VIS}$ clearly depends on the intensity of the visible laser $I_{VIS}$ and has to be calibrated beforehand. In the cases of water droplets containing tryptophan and other bioaerosols like bacteria, pollen gains etc., at the used intensities ($i_{UV}=10^7 W/cm^2$ and $I_{VIS}=10^8 W/cm^2$), $D_{Bio}=0.3$ was measured. In the case of AH and PAH (naphtalene, liquid diesel mixture, soot particles), $D_{NonBio}=0$ was measured.

This large difference clearly evidences the power of the method for discriminating between bioaerosol particles and non-bioaerosol particles. Notice also that this method is insensitive to the pulse-to-pulse fluctuations of the UV laser. Moreover, $F_{UV}/I_{UV}$ provides information about the tryptophan content in the sample.

More generally, when e is a predefined threshold value between 0 and 1, it can be determined that, if D<e, the investigated species or sample is non-biological, or, if D>e, that the investigated species is biological or that the sample contains biological particles.

On the basis of FIG. 1, a rugged, compact (60 cm×60 cm×40 cm), portable instrument was developed, bearing multi-modal capabilities: fluorescence lifetime and a disruptive pump-probe depletion methodology. All these optical data are recorded in real-time and on each individually flowing aerosol particle. In particular the unique advantages of pump-probe depletion spectroscopy for discriminating bio- from non-bio-aerosols was clearly demonstrated.

Several types of aerosols were analyzed with this instrument to assess the discriminability offered by the fluorescence spectrum/lifetime/pump-probe depletion approach. An common aerosol generator (Model 3076 from TSI Inc) and a nebulizer were used to inject different aerosols, like Enterococcus bacteria, diesel droplets, tryptophan particles and humic particles, while the exhausts of two different Diesel cars were used for analyzing non-bio particles emitted by combustion in actual conditions.

FIG. 2 shows typical signals, simultaneously recorded on the pump-probe/lifetime Channel (left column) and on the spectrally resolved fluorescence spectrometer channel (right column). These traces consist of the cumulative signals from 103 individual particles for two species: tryptophan particles and Diesel drops. The plots evidence the fact that linear fluorescence spectroscopy is unable to discriminate between the fluorescence of amino acids (AA) and the fluorescence of polyaromatic hydrocarbons (PAH) in the Diesel drop, as shown in the two right panels. The discrimination is provided by the time resolved, pump-probe signals shown in the left column.

In FIG. 2, the upper left quadrant shows that the tryptophan fluorescence is depleted by typically 20% by the 527 nm pulse, the second pulse in time serving as a reference. In contrast, in the lower left, no depletion is observed for the Diesel droplets. In this portable instrument, typical laser energies are 1 μJ and 10 μJ respectively for the UV and the visible pulses. Additionally, the time-resolved fluorescence displays a short lifetime of less than 5 ns, limited by the instrumental response, for tryptophan and a much longer, 16 ns average for the Diesel mixture. This longer fluorescence lifetime for different. PAHs, ranging from 4 ns to 36 ns, was already studied in the literature in line with these observations.

The approach shown in FIG. 1 and described above can be used for the wide field inspection of samples containing a mixture of biological and non-biological materials. In this case, the PMT 15 would be replaced by a CCD camera, synchronized with the lasers, and the focusing systems 11 and 13 replaced by illumination and viewing optics, respectively, The same approach as in FIG. 1 can also be used for microscopy of samples containing a mixture of biological and non-biological materials. In this case, fluorescence would be detected with a microscope in epi-mode (illumination and detection from one side of the sample) and a scanner would be added to the system.

The approach shown in FIG. 1 can further be used for analyzing water or other liquid contamination, the sample would then consist of a liquid flow or a static cell containing the liquid.

A different example of an application of the invention is the remote identification of pathogen aerosols released in the atmosphere (e.g. terrorist attacks) using a depleted-fluorescence LiDAR. (light detection and ranging) instrument.

FIG. 3 shows this case. The laser 21 is a neodymium-doped yttrium aluminium garnet (Nd:YAG) laser emitting at 1064 nm.

Similar to the first embodiment shown in FIG. 1, the output of laser 21 is frequency-doubled in a nonlinear crystal 22 providing 532 nm radiation (dashed line in the little diagram) and then frequency quadrupled in a second nonlinear crystal 23 providing 266 nm radiation (full line in the little diagram). The UV polarization is set parallel to the visible by a half wave plate 24. The visible radiation (dotted line in FIG. 3) is separated by a first dichroic mirror 25, which transmits 532 nm and reflects 266 nm.

An electro-optic (or acousto-optic) modulator 29 is synchronized with the laser 21 in such a way that it blocks the visible green laser pulse every other pulse. In other words, it blocks the 532 nm visible radiation at half the repetition rate f of the laser 21.

The UV at 266 nm, after being reflected by mirror 27, is then recombined with the chopped visible radiation of 532 nm by a second dichroic mirror 28. The thus produced combined laser pulse sequence contains UV (266 nm) and contains alternating in one case also the 532 nm visible (called "ON") and in the other case no 532 nm visible (called "OFF"). The little diagram in the upper right corner of FIG. 3 shows this.

The laser pulses sequence after mirror 28 then has the following time structure for a laser f=1 kHz repetition rate:

| Time | Pulse |
|---|---|
| t = 0 | UV radiation 266 nm + visible radiation 532 nm, overlapped |
| +1 ms | UV radiation 266 nm only |
| +2 ms | UV radiation 266 nm + visible radiation 532 nm, overlapped |
| +3 ms | UV radiation 266 nm only |
| etc., | |

This laser pulse sequence is focused through a collimating/focusing telescope or other transmitter optics 30 onto the sample 31 and produces the desired fluorescence. Sample 31 here is a "suspect" aerosol cloud, potentially of a mixture of biological and non-biological materials as mentioned above, standing in the atmosphere at a distance R from the LiDAR.

The backwards emitted fluorescent light is collected by a Newtonian telescope 32, focused on an iris for adapting the field of view, expanded and collected, respectively, by lenses 33 to allow splitting into two channels by a dichroic mirror 34 which reflects the UV of 266 nm and transmits the fluorescence at 350 nm. The UV channel, consisting of a filter 36 centered at 266 nm, another lens 33, and a first PMT 39 records the backscattered UV signal EUV (in number of photons) as a function of time (i.e, distance R=ct with c the light velocity). The fluorescence channel, consisting of a filter 35 centered at 340 nm, another lens, 33, and a second PMT 37, records the fluorescence E(R) in number of photons as a function of distance R also for the ON and OFF laser pulses separately. Both signals from PMT 37 and PMT 39 are recorded as a function of time in the data acquisition system 38. From the inversion of the three signals $E_{ON}(R)$, $E_{OFF}R)$, and $E_{UV}(R)$, one derives an assessment of the probability that the suspect cloud is mainly formed by biological substances or "harmless" AH. This could be applied, e.g., when checking a typical bioterrorisin threat consisting of sprays of pathogen bacteria, like anthrax, yersina pestis, or liquid drops containing viruses.

FIG. 4 finally depicts schematically a third implementation of an apparatus according to the invention, this time using a continuous wave (CW) laser. The aim of this embodiment is to detect and quantify bacterial contamination of liquids like water.

Figure 4:
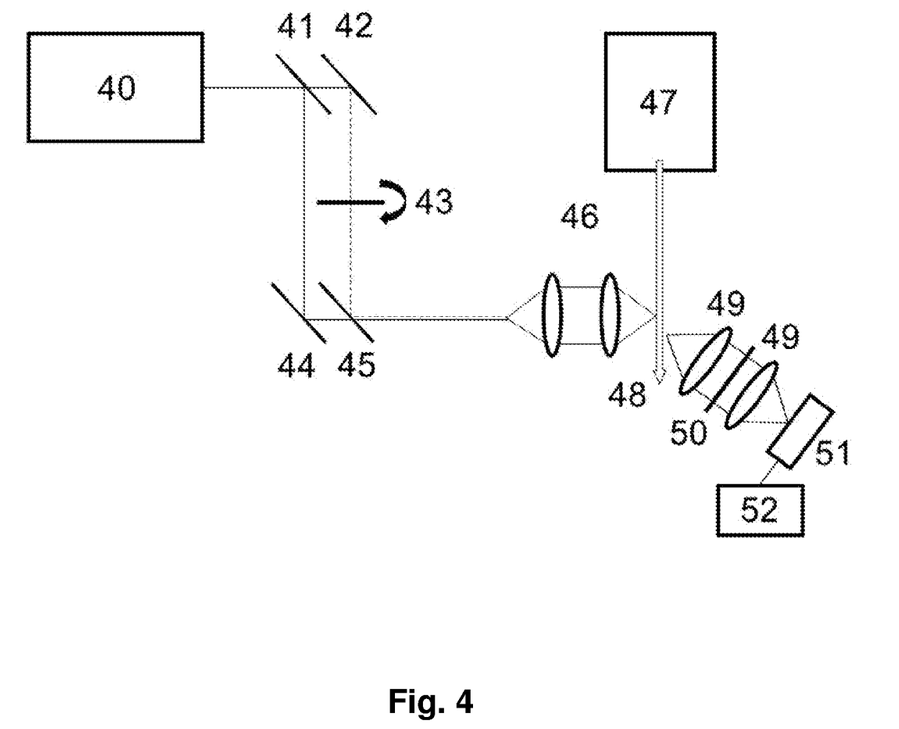
FIG. 4 is a schematic of a third apparatus according to the invention using a CW laser source.

Here, a flow of 1 m/s of liquid in a tube and a sapphire nozzle 47 provided as a liquid jet 48 is subjected to a measurement spot with a size of 50 μm. A typical bacterium is about 1 μm in diameter, so very small in comparison.

From measurements conducted, it was found that laser powers of 100 kW/cm² for the pump section and 1 MW/cm² forhe probe section leads to a detectable depletion of only about 3%. These are, however, single shot measurements, i,e, a single fluorescence depletion cycle/particle.

In the present example with a CW laser, each particle would experience an illumination time of 50 μm/1 m/s=50 μs. Assuming 50 ns for the fluorescence cycle, which is a conservative value, this leads to an improvement in signal-to-noise ratio (SNR) of roughly the square root of 1000, i.e. a factor of about 30 in SNR. The intensities could therefore be reduced by about 30, resulting in approximately 3 kW/cm² for the pump section and 30 kW/cm² for the probe section. On a spot size of 50 μm, this corresponds to reasonable CW laser powers of 60 mW and 600 mW, respectively. To be on the safe side, standard CW lasers providing 1 W of UV and 10 W of visible (green) appear to be a suitable choice.

FIG. 4 is a schematic illustration again. Pulse source is a diode-pumped solid-state continuous wave (DPSS CW) laser 41 whose laser emission occurs at both 266 nm and 532 nm after frequency doubling and quadrupling (not shown). The visible radiation (dotted line in FIG. 4) is separated by a first dichroic mirror 41, which reflects 266 nm and transmits 532 nm. A mirror 44 redirects the 266 nm UV and a mirror 42 which redirects the 532 nm visible radiation.

The 266 nm UV beam is chopped by an electro-optic modulator 43 which is synchronized with the laser 40, blocking the 532 nm UV laser pulse every half of the time within the measuring cycle of 50 μs. In other words, it provides a square modulated signal with a 50%/50% duty cycle. Lock-in detection might be implemented to improve the signal-to-noise ratio (SNR).

The chopped 532 nm laser beam is recombined with the 266 nm radiation by a second dichroic mirror 45. The recombined beam is focused by lenses 46 onto the 50 μm measurement spot of the liquid jet 48.

Fluorescence reading is done through lenses 49 with an intermediate spectral filter 50 transmitting the fluorescence at 340 nm to a photomultiplier (PMT) detector 51, connected to the acquisition computer 52.

The embodiment shown in FIG. 4 and described above functions in the following way. As in the previous embodiments, the depleted and undepleted fluorescence signals, representing the first and second halves of the measuring cycle, resp., are used to calculate the depletion ratio D and the total fluorescence, so that the concentration of bacteria flowing in the jet can be assessed, and discriminated from non-biological organic, but fluorescing, species.

The above detailed description of the function and of various embodiments of the present invention permit a person skilled in the art to devise further implementations without departing from spirit and scope of the present invention.

What is claimed is:

1. A method for non-destructively discriminating between a biological species and a non-biological species, or a sample containing biological particles and a sample containing only non-biological particles, by subjecting said species or said sample to radiation and deriving discriminating evidence from fluorescence emitted by said species or said sample, comprising:
   subjecting said species or said sample to a first radiation of essentially simultaneous visible and UV and recording an emitted first fluorescence intensity $F_{UV+VIS}$,
   subjecting said species or said sample to a second radiation of sole UV and recording an emitted second fluorescence intensity $F_{UV}$,
   both said first and second radiations lasting longer than the vibronic coherence time of subjected species or samples,
   comparing the recorded first and second fluorescence intensities and obtaining a determination from the variance of said fluorescences whether said species is biological or non-biological or whether said sample contains biological particles or not.

2. The method according to claim 1, wherein the first radiation of essentially simultaneous visible and UV is applied to the species or sample in a first time period alternating with the application of the second radiation of sole UV in a second time period.

3. The method according to claim 1, wherein the first and the second radiation are applied alternatingly for several nanoseconds (ns), preferably about 5 ns.

4. The method according to claim 1, wherein the visible part within the first radiation is temporally delayed vis-a-vis the UV part.

5. The method according to claim 1, wherein a pause of several nanoseconds (ns), preferably up to about 30 ns, is provided between application of the first and the second radiation, so that the sequence of laser pulses has the following time structure:

| | |
|---|---|
| t = 0 | UV radiation + visible radiation, overlapped |
| t = +20-30 ns | UV radiation only. |

6. The method according to claim 1, wherein the following repetitive sequence of first and second radiations is applied to the species or sample, at given times t:

| | |
|---|---|
| t = 0 | UV radiation + visible radiation, overlapped |
| t = +1/f | UV radiation only |
| t = +2/f | UV radiation + visible radiation, overlapped |
| t = +3/f | UV radiation only, |
| etc., | |
| where f is a repetition rate of the laser. | |

7. The method according to claim 1, wherein the determination is obtained from calculating the depletion ratio D $$D=(F_{UV}-F_{UV+VIS})/F_{UV}$$

wherein $F_{UV+VIS}$ is the first fluorescence intensity and $F_{UV}$ is the second fluorescence intensity, and
if D<e, determining that the species or the sample is non biological, or
if D>e, determining that said species is biological or that said sample contains biological particles, resp.
where e is a predefined threshold value between 0 and 1.

8. The method according to claim 1, wherein the first radiation is visible radiation of 527-532 nm overlapped with UV radiation of 263-266 nm, and the second radiation is UV radiation of 263-266 nm.

9. The method according to claim 1, wherein
both the first and second radiations are generated by a single solid state laser.

10. The method according to claim 1, wherein
both the first and second radiations are produced by a continuous wave (CW) solid state laser, the visible radiation being intermittently blocked.

11. An appparatus for non-destructively distinguishing a biological species from a non-biological species, or a sample containing biological particles from a sample containing only non-biological particles, including means for generating radiation to which said species or said sample is exposed and means for gathering fluorescence emissions from said species or said sample,
comprising:
a laser with optical means for generating visible and UV radiation,
first optical path means for generating a first beam to be applied to said species or sample, said first beam comprising visible and UV radiation,
second optical path means for generating a second beam to be applied to said species or sample, said second beam consisting of sole UV radiation,
at least one of said optical path means including means for delaying or modulating said first or said second beam,
both said first and second beams being applied to said species or said sample for a time longer than the vibronic coherence time of said species or sample,
means for identifying and recording a first emitted fluorescence intensity when said species or sample is exposed to said first beam and a second fluorescence intensity when said species or sample is exposed to said second beam, and for determining from the recorded first and second fluorescence intensities whether said species is biological or non-biological or whether said sample contains biological particles or not.

12. The apparatus according to claim 11, wherein
the means for identifying and recording comprises a spectral filter for rejecting any diffuse visible and/or UV radiation, a photomultiplier tube, and a computerized data acquisition system.

13. The apparatus according to claim 11, comprising
a pulsed laser, in particular an Nd:YLF laser, whose emission is frequency-multiplied by optical means to provide both the visible radiation and the UV radiation,
the first optical path means including first optical means, in particular a dichroic mirror, for separating a visible beam from a UV beam,
a beam splitter for splitting said UV beam into a first UV beam and a second UV beam,
second optical means, in particular a mirror (9), for recombining said visible beam with said first UV beam, thus providing the first beam of visible and UV radiation,
third optical means constituting the means for delaying or modulating, in particular a plurality of mirrors, for delaying said second UV beam, thus providing the beam of sole UV radiation impacting intermittently on the species or sample, timely offset from the impact of said first beam of visible and UV radiation.

14. The apparatus according to claim 11, in particular for detecting and quantifying bacterial contamination in an aerosol cloud of biological and non-biological materials, comprising
a pulsed laser, in particular an Nd:YAG laser, and optical means for frequency-multiplying a laser's emission to provide both the visible radiation and the UV radiation,
first optical means, in particular a dichroic mirror, for separating a visible beam from a UV beam,
a modulator, in particular an electro-optic or acousto-optic modulator, for modulating said visible beam,
second optical means, in particular a mirror, for recombining said modulated visible beam with said UV beam, thus providing the first beam of visible and UV radiation alternating with the beam of sole UV radiation,
third optical means for collecting radiation emitted from the sample, said third optical means including a first channel for recording the fluorescense intensities and a second channelrecording any backscattered, especially UV, radiation, and
means for determining from said recorded fluorescence intensities and said recorded backscattered radiation whether the sample is contaminated or not.

15. The apparatus according to claim 14, wherein
the modulator is designed to block the visible beam at half the repetition rate of the pulsed laser.

16. The apparatus according to claim 14,
being designed as LiDAR (light detection and ranging) instrument for detecting and quantifying bacteria or other biological materials in a distant aerosol cloud.

17. The apparatus according to claim 11, in particular for detecting and quantifying bacterial contamination of a liquid sample by illuminating a spot of a jet of said liquid sample for a given time period, comprising
a continuous-wave laser, in particular a DPSS CW laser, whose emission is frequency-multiplied to provide both the visible radiation and the UV radiation,
first optical means, in particular a dichroic mirror, for separating a visible beam from a UV beam,
a modulator, in particular an electro-optic or acousto-optic modulator, for modulating said visible beam,
second optical means, in particular a mirror, for recombining said modulated visible beam with said UV beam, thus providing the first beam of visible and UV radiation for a first illumination period within a measuring cycle alternating with the beam of sole UV radiation for a second illumination period.

18. The apparatus according to claim 17, wherein
the measurement spot size of the jet is selected to about 50 μm,
the measuring cycle time is selected to about 50 μs, and
the modulator is designed to block the visible radiation half of the time within said measuring cycle.

* * * * *